United States Patent
Dezzani

(12) 
(10) Patent No.: US 6,228,123 B1
(45) Date of Patent: May 8, 2001

(54) VARIABLE MODULUS PROSTHETIC HIP STEM

(75) Inventor: Michael Massino Dezzani, Lakeville, MA (US)

(73) Assignee: Depuy Orthopaedics, Inc., Warsaw, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/136,349

(22) Filed: Aug. 19, 1998

(51) Int. Cl.$^7$ ............................................. A61F 2/36
(52) U.S. Cl. ........................... 623/23.32; 623/23.18; 623/23.15
(58) Field of Search ................ 623/23, 22, 18, 623/16, 11, 12, 15, 26, 32

(56) References Cited

U.S. PATENT DOCUMENTS

| | | |
|---|---|---|
| 3,893,196 | 7/1975 | Hochman .................. 3/1.91 |
| 4,221,623 | 9/1980 | Heissler et al. .............. 156/169 |
| 4,266,302 * | 5/1981 | Tornier ..................... 623/23 |
| 4,356,571 | 11/1982 | Esper et al. ................. 3/1 |
| 4,446,579 * | 5/1984 | Inamori et al. .............. 623/23 |
| 4,532,660 | 8/1985 | Field ....................... 623/18 |
| 4,681,590 | 7/1987 | Tansey ..................... 623/23 |
| 4,683,018 | 7/1987 | Sutcliffe et al. ............. 156/196 |
| 4,714,467 | 12/1987 | Lechner et al. .............. 623/16 |
| 4,743,263 * | 5/1988 | Petrtyl et al. ............... 623/23 |
| 4,892,552 | 1/1990 | Ainsworth et al. ............ 623/23 |
| 4,902,297 | 2/1990 | Devanathan ................. 623/16 |
| 4,938,771 | 7/1990 | Vecei et al. ................. 623/23 |
| 4,978,360 * | 12/1990 | Devanathan ................. 623/66 |
| 4,997,444 | 3/1991 | Farling ..................... 623/16 |
| 5,002,579 | 3/1991 | Copf et al. ................. 623/23 |
| 5,064,439 | 11/1991 | Chang et al. ............... 623/66 |
| 5,141,521 | 8/1992 | Wenner .................... 623/23 |
| 5,163,962 | 11/1992 | Salzstein et al. ............. 623/23 |
| 5,181,930 | 1/1993 | Dumbleton et al. ........... 623/23 |
| 5,192,330 | 3/1993 | Chang et al. ............... 623/22 |
| 5,397,365 | 3/1995 | Trentacosta ................. 623/18 |
| 5,522,904 | 6/1996 | Moran et al. ............... 623/22 |
| 5,591,233 | 1/1997 | Kelman et al. .............. 623/16 |
| 5,609,638 | 3/1997 | Price et al. ................. 623/18 |
| 5,807,407 * | 9/1998 | England et al. .............. 623/16 |

* cited by examiner

Primary Examiner—Dinh X. Nguyen
Assistant Examiner—Alvin Stewart
(74) Attorney, Agent, or Firm—Nutter, McClennen & Fish, LLP

(57) ABSTRACT

A prosthetic stem insertable in an intramedullary cavity to support an articulation component includes a proximal neck portion and a distal root portion. The proximal neck is solid metal and extends for a length effective to reach into the cavity and couple to surrounding bone for load bearing engagement therewith, while the distal root portion includes a stranded cable which fills the bone cavity but flexes to avoid significant transfer of bending stresses. The cable is tightly bunched at its junction with the neck, providing a transitional degree of stiffness to its distal part which is significantly more flexible and bends to accommodate natural displacement of the surrounding bone. The prosthesis may be formed of a compatible metal such as titanium, cobalt chromium, stainless steel or the like. The prosthesis has a section modulus characterized by three distinct regions. The proximal end region has the largest cross section and presents a stiff modulus of solid material, while the distal region is composed of strands and presents a flexible bending stiffness. An intermediate region of relatively short length where the cable attaches to the upper portion has a bending modulus that changes quickly from fairly stiff to flexible. The location of this portion may be varied by changing the relative lengths of the proximal solid and distal cable portions thus determining or limiting to a small local region the area of bone which may experience any stress shielding. The stiffness of the cable may also be varied by use of different gauge wires or the addition of welds or circumferential bands. In various embodiments, the cable may be entirely enclosed within a surrounding shell, may have its distal end crimped within a surrounding ring or cup, or may have its filaments welded or otherwise fused or bonded together at one or more regions. In one embodiment the cable is formed of asymmetric fibers which run parallel to each other to provide a bending modulus that is stiffer in one plane than in the transverse direction.

13 Claims, 2 Drawing Sheets

VARIABLE MODULUS PROSTHETIC HIP STEM

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates to an improved prosthetic bone termination, such as a hip stem prosthesis and to a method of imparting desirable mechanical properties to such a stem. It also relates generally to other bone prostheses having a prothesis stem implant portion.

BACKGROUND OF THE INVENTION

A great many constructions have been proposed for the stem portion of the femoral component of a hip prosthesis. This component attaches to the proximal end of the femur, replacing the natural bone termination, and generally carries the ball of the prosthetic hip joint, which is either separately attached or integrally formed with the stem. The stem fits into the intramedullary canal of the femur, which is generally prepared by resection of the bone end, and reaming or broaching a bore to remove a portion of the central bone tissue. In addition to a number of specialized proprietary or modular constructions, these stems may have one of several overall architectures. One of these involves a completely solid stem having a shaped shoulder portion which fits very precisely into a corresponding prepared cavity that is first machined in the end of the proximal femur. Such stems are made in a discrete number of sizes, and during surgery special milling or boring tools are used to form precise cutouts in the femoral spout to accommodate the contour of the prosthesis, which is driven in to an exact fit with the bone, providing a fairly rigid and tightly fitting attachment without cement. Another form of stem is intended to be fixed primarily by setting it in bone cement. Stems of this type may have somewhat smaller dimensions and shoulder portion, allowing a space between the bone opening and the prosthesis to be filled with bone cement. Each of these constructions involves a strong metal stem, which takes over a significant share of the load carried by the femur.

It has long been known that the provision of a fairly rigid metal prosthesis can result in loss of original bone. This occurs even in the absence of disease, because the processes of bone growth and bone resorption both occur continuously. Bone growth tends to increase in response to active strain in the bone itself, whereas resorption occurs normally at a moderate level, and may increase in dependence upon a number of metabolic or hormonal factors of the individual. Since femoral stem components are generally designed to assure that during their implanted life breakage does not occur, most constructions are quite rigid, so that they carry much of the load normally borne by an intact femur. This results in stress shielding. That is, some regions of the bone experience less strain, causing certain areas of the femur to experience lesser growth, leading to a net resorption, or loss of bone mass. Since many hip stems are designed to be driven into a prepared bone canal and intimately connect to the surrounding bone, care must be taken that the prosthesis itself not assume too great a proportion of the bearing load.

This problem has been addressed by designing hip stems to have a more flexible bending stiffness in their distal end. The reduction in bending stiffness is achieved, for example by employing thinner bodies or by providing slots in the stem. The latter approach also aids in initial fitting of the device.

Another commonly encountered problem is that the distal portion of the prosthesis may bear against the inner surface of the bone and cause pain. This occurs most commonly when the prosthesis fails to anchor completely to surrounding bone at the shoulder area, or when anchoring bone in the shoulder area degenerates or is resorbed, so that some wobble of the stem shaft occurs with respect to the bone. It may also occur when misalignment of the stem within the bone canal results in excessive pressure in a localized region of contact at the stem's distal end.

In addition to the foregoing effects, various individual reactions or bone conditions may result in less than optimal fixation of either type of existing stem, or may result in bone loss or bone pain after the stem has been implanted for some time. In the latter case, the condition may have causes other than the altered apportionment of load bearing between the stem and the natural bone, so that one cannot expect to eliminate such complications simply by altering the shape or stiffness of the stem/comnponent. Nonetheless, the prosthesis size, stiffness and overall shape for achieving basic mechanical properties, appear to lie at the root of several common problems.

Accordingly it would be desirable to provide a stem component of different mechanical characteristics.

SUMMARY OF THE INVENTION

This is achieved in accordance with a basic embodiment of the invention by providing a prosthetic stem for insertion into an intramedullary cavity to support an articulation component, wherein the stem includes a proximal neck portion and a distal root portion. The proximal neck is solid metal and extends for a length effective to reach into the cavity and stiffly couple to surrounding bone for load bearing engagement therewith. The distal root portion on the other hand is composed of a stranded cable which fills the bone cavity but flexes to limit transfer of bending stresses to the bone. Preferably the cable is tightly bunched at its junction with the neck, providing a degree of stiffness and columnar support at the junction region. However distally thereof, the cable is significantly more flexible. It bends to accommodate natural displacement of the surrounding bone, and it transmits a controlled or limited amount of bending stress when load is applied at the proximal end to assure that the normal bone is not bypassed for transmission of load to the distal region of the proximal femur. The prosthesis may be formed of a compatible metal such as titanium, cobalt chromium, stainless steel or the like, and it has a section modulus characterized by three distinct regions. The proximal end region presents a stiff section modulus of solid material while the distal region presents a flexible section modulus. An intermediate region of relatively short length where the cable attaches to the upper portion has a bending modulus that changes quickly from stiff to flexible. The location of this portion may be varied by changing the relative lengths of the proximal and distal portions, and to a lesser extent, by binding or fusing the cable at on or more positions to locally increase bending stiffness. In various embodiments, the cable may be entirely enclosed within a surrounding shell, or may be uncovered but have its filaments welded or otherwise fused or bonded together at one or more positions along its length. The cable may be attached to the proximal solid body portion by welding, or by crimping the solid portion around the cable. Similarly, the cable may have its distal end crimped within a surrounding ring or cup. In one embodiment, the cable is formed of parallel strands having an asymmetric cross-section, such as an ovaloid section. The strands run parallel to each other to provide a bending modulus that is stiffer in one plane than in the transverse direction. The strands of the cable may be about one to ten mils in cross-dimension.

BRIEF DESCRIPTION OF THE DRAWINGS

These and other features of the invention will be understood from the description herein and claims appended hereto, taken together with the drawings showing illustrative embodiments of the invention, wherein:

DETAILED DESCRIPTION OF ILLUSTRATIVE EMBODIMENT

Figure 1:
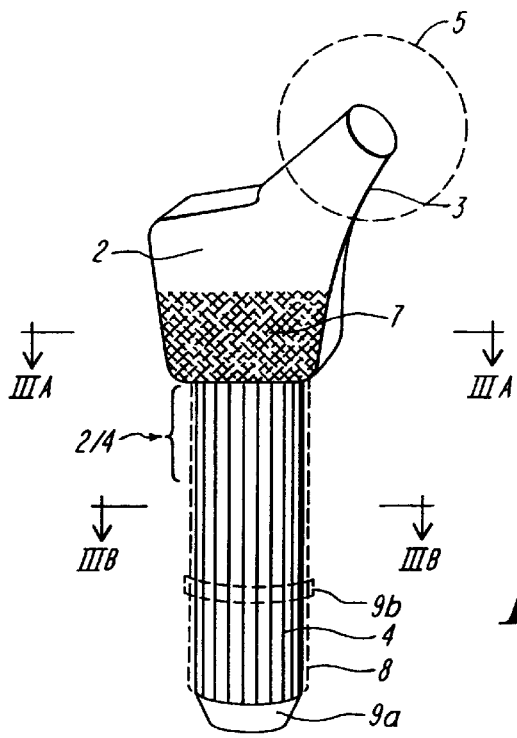
FIG. 1 is a conceptual drawing of a hip prosthesis stem of the present invention.

FIG. 1 by way of illustration shows one embodiment of the invention applied to a hip prosthesis 10. As shown therein, the prosthesis 10 includes a stem portion 2, 4 which fits within the proximal femur, and extends to a termination at its proximal portion shown as a post 3 for receiving a ball 5, indicated by dashed lines, forming a joint wear surface for articulating contact with the acetabular cup. The upper or proximal portion 2 may have a textured shoulder as indicated at 7, with surface relief or porosity features known in the art to enable rigid intergrowth of new bone to couple the prosthesis to the existing femur over time after implantation. As further shown in FIG. 1, the upper portion or shoulder and articulation supporting proximal end 2 is a generally continuous solid member while the distal region 4 is comprised of a plurality parallel strands of material, forming a cable. The strands may be round, having isotropic bending stiffness, and may be bundled in a bundle of circular cross-section so that the cable as a whole has isotropic bending stiffness. In some embodiments an enclosure 8 (shown in phantom) may cover the cable, and means 9a, 9b . . . may be provided binding the cable together at plural positions along its length.

In general, applicant contemplates that both portions 2,4 are formed of metal, of a material such as ASTMF-136, titanium aluminum vanadium alloy, ASTMF-75, cobalt chromium or other alloy of a type customarily used for forming prosthetic stem members. Portion 2 may be of a relatively large fitted shape, for example having a collar to define its insertion depth, and/or a curved or cylindrical surface in the spout region configured for directly contacting and fitting to a prepared bone surface; the provision of surface texture in this region promotes relatively quick and properly aligned fixation to the femur by natural bone intergrowth. However, alternatively, the prosthesis may be of somewhat smaller size, and be configured for setting in bone cement to secure fixation. The filament or cable portion 4 is also made of one of the foregoing metals; however, these are in a form such as strands of wire, which may be formed or processed, for example, by drawing, rolling, annealing, tempering, and various passivation processes, to assure that the strands are strong, integral and do not corrode. The stem portion 4 is considerably smaller than the shoulder portion, and in this embodiment is sized similarly to the stem of a cemented prosthesis, to be of relatively small diameter for fitting fully within the prepared bone canal with ample clearance. Thus as an initial matter, the stem root portion 4 is of lesser cross-section than the upper portion 2, and is formed of metallic strands, which as illustrated extend for a length of several inches or more into the bone cavity without however, directly wedging against or broaching the bone.

Thus, in accordance with a principal aspect of the present invention, a stem portion of an implanted prosthesis comprises a proximal solid body configured to fit into a bone for anchoring in a bone ending, and a distal stranded or cable extension body attached thereto and configured to extend for a substantial length past the solid body within the bone canal, and having a second modulus substantially less than that of the proximal body. The stem portion is formed of plural separate strands or wires, which are anchored at least at the solid end and extend as a space-filling but bendable root. The strands are preferably bundled together or enclosed so that while they may move with respect to each other, broken strands or wear debris do not escape or migrate within the bone canal.

Figure 3A:
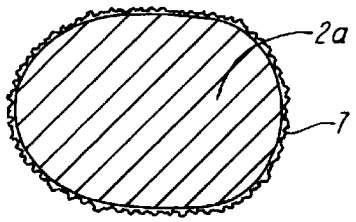
FIGS. 3A and 3B illustrate cross-sectional views of the stem of FIG. 1.
Figure 3B:
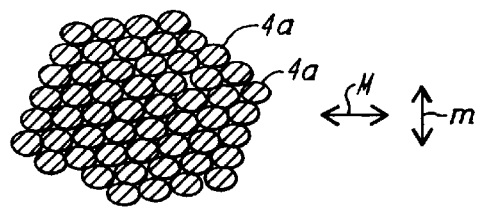

FIGS. 3A and 3B illustrate sections taken through the solid portion 2 and the cable portion 4, respectively, of the prosthesis 10 of FIG. 1. As shown in FIG. 3A, the solid portion has an interior 2a of substantially homogeneous material which may be cast metal or the like, and one or more regions 7 on its outer surface which are formed as textured or porous material. The cable portion 4 by contrast, shown in FIG. 3B, is comprised of a plurality of strands 4a extending parallel to each other in space-filling contiguity to fill a generally densely packed closed contour which as shown in FIG. 3B is roughly oval in cross-section. As further shown in that figure, each strand may itself be oval in cross-section having a major axis M and a minor axis m. As a result of this fiber geometry, each fiber has a bending stiffness which is greater in the left-right direction (as shown along the axis M which is the medial lateral direction for the illustrated hip stem) than in the front-to-back direction. These oval fibers may be bundled quite naturally into a generally ovaloid contour. The invention however, also contemplates perfectly symmetrical, circular cross-section, filaments, and filaments of such shapes bundled into a bundle of generally circular, oval or other cross-section.

In the construction of the bundle 4, the proximal ends of the fibers 4a are rigidly affixed within the solid member 2. This may be done, for example, by crimping the body 2 about the cable, or by resistance welding the two together at the tops of the strands, or by inert gas welding or fusing together of the fiber ends, followed by machining and attaching the unified assembly to the body 2. For this purpose, the solid shoulder 2 may have a counterbored opening at its bottom into which the cable is fitted. Furthermore, while not necessary to the invention, the distal ends of the wires constituting cable 4 may be joined together, for example by electron beam welding the ends of the cable, so that all these strands fuse together to a depth, e.g., of approximately one millimeter. Such joining may also be accomplished by crimping or interference fitting a solid circumferential band about the strands, or by a combination of crimping and welding. One or more additional bands may also be placed about intermediate portions of the cable along its length. The additional bands prevent migration of any strands or segments of strands which may erode or break off during the lifetime of the implant. In addition, each tight or welded band limits strand-to-strand slippage during bending, increasing the distal stem bending stiffness in the region of the band or weld.

Preferably the cable is formed of metal strands about one to five mils in diameter, the number of strands being such that the entire bundle has a dimension comparable to or smaller than the one or two centimeter diameter of a conventional solid stem prosthesis. This construction provides a section modulus in region 4 which may be substantially less, for example one third to three quarters or more less than the distal section modulus of a conventional solid stem of a similarly sized prosthesis. Preferably, the cable is configured to have a bending stiffness or section modulus less than that of the bone into which it fits, thus assuring that the bone continues to experience a natural level of strain. Furthermore, the distal stem portion 4 does not need to be configured for initial fixation in the bone. Thus, for example while it may set into a cement filled area of the bone, it possesses neither bone gripping protrusions, nor a surface texture to promote rigid cement adhesion or bone attachment. Indeed, as the surrounding bone bears a load, the stem portion 4 essentially hangs within the bone cavity and the smooth surface of fibers 4 may allow the cable portion to move longitudinally with respect to surrounding bone by sliding motion on a micro-scale proportional to the degree of bone compression, displacement or strain elongation around it. Thus both the bending modulus and the sectional modulus of the prosthesis are substantially less than those of a solid member and its degree of connection or fixation to the surrounding bone in the distal region is small or even negligible during initial fixation or shortly thereafter.

Figure 2:
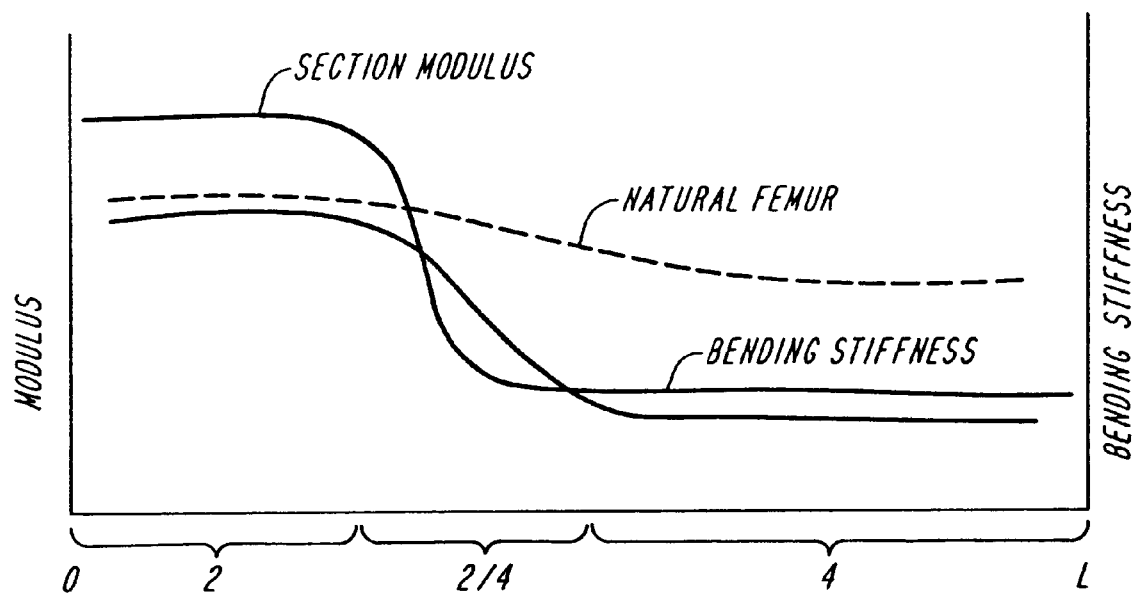
FIG. 2 shows a conceptual graph of stiffness of the stem of FIG. 1.

FIG. 2 shows a conceptual graph of the bending stiffness and the sectional modulus of the stem of FIG. 1, both plotted in arbitrary units on the same graph. For purposes of illustration, the regions of the prosthesis are plotted from zero at the proximal end to its length L, proceeding from the shoulder portion 2 to the distal end of the cable 4, with the initial portion of cable at its region of attachment to body 2 denoted by the hybrid legend 2/4.

By way of comparison in FIG. 2, the corresponding section modulus of the natural femur is shown as dashed line graph, superposed over the stiffness and modulus graphs of the prosthesis. As shown in that figure, both the bending stiffness and section modulus of the prosthesis are significantly higher than that of the natural femur in the shoulder region 2 and both are substantially lower in the cable region 4. As a result, a major portion of bone loading and the stress of bending are born by the bone itself in the distal region. As further shown, the section modulus diminishes slightly in the distal region of the solid shoulder 2, and then drops sharply in the initial region 2/4 of the cable 4, to provide a transition between the stiff shoulder and the flexible cable. Similarly, the bending stiffness undergoes a decline with a somewhat less abrupt transition between regions 2 and 4, which is due primarily to the increased coupling between longitudinal strain and the other directions of stress acting on the fibers in the region where they are immobilized by crimping or welding at the end. In each case however, the mechanical stiffness or modulus lies appreciably below that of the surrounding bone, so that an increased proportion of the strain loading is born by the natural bone in the distal region of the stem.

The foregoing construction allows a certain degree of flexibility in optimizing the mechanical properties of the distal stem. In particular, by providing a cable comprised of a relatively few strands of relatively large diameter wire, the stiffness of the cable is increased to a point where the stem bears a significant portion of the bending load. These features may be used to form a prosthesis which bears a greater portion of the load. Conversely, by using a number of relatively small wires, e.g., 1 to 3 mil strands, the stiffness or modulus is greatly reduced. Thus, the cable portion may be configured in flexibility to an extent that the distal stem provides a stimulating level of strain transmission to the distal femur, without assuming a substantial portion of the load bearing function thereof. Furthermore, by changing the relative length of the solid portion 2, the prosthesis is readily modified to limit stress shielding to the proximal femoral end, or to extend the shielding somewhat farther. Significantly, however, the cable has very limited columnar or vertical support strength, so the stem cannot entirely bypass the structural function of the intervening bone. This factor is expected to prevent the occurrence of patchy bone loss below the point of attachment the stem.

It will be appreciated that the foregoing description focuses on structure rather than specific implementations of the invention, which is understood to be carried out using known materials. However, it will be understood that by using a material such as cobalt chrome, a relatively stiffer structure is obtained than with a titanium alloy. Further, the precise embodiments found optimal for implantation will be partly determined from actual use. The cable portion 4 may be found to be desirably implemented with a different material than the shoulder portion 2 in order to adjust higher or lower the stiffness or modulus within the general contours of the profile reductions illustrated in FIG. 2. Furthermore, the mode of attachment, enclosure or banding together of the various components formed separately is subject to variation. The invention, while described above with reference to a hip stem component, may be advantageously implemented in other joint or junction prostheses. Thus, for example, it may be applied to form a cable stem for a tibial platform or tibial component center post, or to form all or a portion of a spike-like member intended for internal reinforcement of a splice in a long bone at a break, joining two pieces of a fractured long bone. In the latter case, the provision of an elongated but flexible member facilitates insertion into the bone fracture ends, with less displacement of the bone or resection of surrounding tissue. Thus, the cable body may be practiced both to achieve greatly lowered modulus, and to produce flexible fixation members. Other changes, modifications and adaptations of the invention will occur to those skilled in the art, and all such changes and adaptations are considered to lie within the scope of the invention, as set forth in the claims appended hereto.

What is claimed is:

1. A prosthesis of the type including at least a stem having a distal root portion for insertion into an intramedullary cavity and a proximal portion for supporting a head or junction component wherein said proximal portion is solid and extends into the intramedullary cavity for a length effective to couple to surrounding bone for stress-transmissive engagement therewith, and said distal root portion extends from said proximal solid portion and includes a cable comprising a plurality of strands extending in a generally densely packed space-filling contiguity centrally in said cavity, the strands being selected to achieve a bending modulus of the distal root less than a bendibg modulus of said proximal portion and the natural femur such so to provide a stimulating level of strain transmission to distal bone while limiting load bearing function and thereby avoid stress shielding.

2. A prosthesis according to claim 1, wherein at least said proximal portion is formed of a metal selected from among titanium, cobalt chromium, stainless steel and compatible metal.

3. A prosthesis according to claim 1, wherein the proximal solid portion has a first bending stiffness A and the distal root portion has a bending stiffness B wherein B<<A.

4. A prosthesis according to claim 3, further having an intermediate portion between said proximal neck and said distal root portion, said cable extending in said intermediate portion, and having a bending stiffness C such that B<C<A.

5. A prosthesis according to claim 3, wherein said cable is formed of strands having anisotropic bending stiffness.

6. A prosthesis according to claim 3, wherein said cable is bundled into cross-section having anisotropic bending stiffness.

7. A prosthesis according to claim 3, wherein said cable is formed of strands having isotropic bending stiffness.

8. A prosthesis according to claim 3, wherein said cable is bundled into cross-section having isotropic bending stiffness.

9. A prosthesis according to claim 3, wherein said cable is crimped into said solid proximal portion.

10. A prosthesis according to claim 3, wherein said cable is welded to said solid proximal portion.

11. A prosthesis according to claim 3, wherein said cable is bound together at plural positions along its length.

12. A prosthesis according to claim 3, wherein said cable is covered by an enclosure along its length.

13. A method of forming a prosthesis for a bone ending, such method comprising the steps of providing a solid member having a distal end shaped to extend into a prepared bone opening and anchor in load-transmissive engagement with surrounding bone, said member having an articulation surface or means for receiving an articulation surface at a proximal end, and providing a cable extending from the distal end of said solid member, said cable being fixedly attached to the solid member and comprising a plurality of strands extending in a generally densely packed space-filling contiguity centrally in the bone opening wherein the step of providing a cable includes selecting the strands to achieve a bending modulus of the distal root less than a bending modulus of said proximal portion and the natural femur such as to provide a stimulating level of strain transmission to distal bone while limiting load bearing function and thereby avoid stress shielding.

* * * * *